US006999866B2

(12) United States Patent
Noda

(10) Patent No.: US 6,999,866 B2
(45) Date of Patent: Feb. 14, 2006

(54) COMBUSTION CONTROL SYSTEM AND METHOD FOR SPARK-IGNITION INTERNAL COMBUSTION ENGINE

(75) Inventor: Toru Noda, Yokohama (JP)

(73) Assignee: Nissan Motor Co., Ltd., Yokohama (JP)

( * ) Notice: Subject to any disclaimer, the term of this patent is extended or adjusted under 35 U.S.C. 154(b) by 37 days.

(21) Appl. No.: 10/828,458

(22) Filed: Apr. 21, 2004

(65) Prior Publication Data

US 2004/0220720 A1 Nov. 4, 2004

(30) Foreign Application Priority Data

May 2, 2003 (JP) ............................ 2003-126869

(51) Int. Cl.
F02D 41/02 (2006.01)
F02P 5/152 (2006.01)

(52) U.S. Cl. ............. 701/111; 123/406.29; 123/406.37; 73/117.3

(58) Field of Classification Search ................ 701/111, 701/102, 101; 123/406.29, 406.16, 406.37; 73/117.3

See application file for complete search history.

(56) References Cited

U.S. PATENT DOCUMENTS

| 4,694,800 A |   | 9/1987 | Morita |
| 4,846,129 A |   | 7/1989 | Noble |
| 5,206,809 A | * | 4/1993 | Iwakiri et al. ............... 701/111 |
| 5,386,722 A | * | 2/1995 | Meyer et al. ............... 73/117.3 |

FOREIGN PATENT DOCUMENTS

| JP | 7-332149 A | 12/1995 |
| WO | WO 99/06683 A1 | 2/1999 |

OTHER PUBLICATIONS

Yasuo Takagi et al., "An Analytical Study on Knocking Heat Release and its Control in a Spark Ignition Engine", SAE Technical Paper Series, No. 880196, Feb. 29, 1988, pp. 1-10.

* cited by examiner

Primary Examiner—Hieu T. Vo
(74) Attorney, Agent, or Firm—Foley & Lardner LLP

(57) ABSTRACT

A combustion control system for a spark ignition internal combustion engine, is configured to detect engine operating conditions, predict, based on the detected engine operating conditions, an autoignition timing of an end gas and an amount of heat released due to autoignition of the end gas, calculate a knock intensity from the autoignition timing and the amount of heat released due to the autoignition, and control combustion in the engine in such a manner that the knock intensity is lower than or equal to a specified intensity limit.

22 Claims, 8 Drawing Sheets

SAE 880196(1998)

SAE 880196(1998)

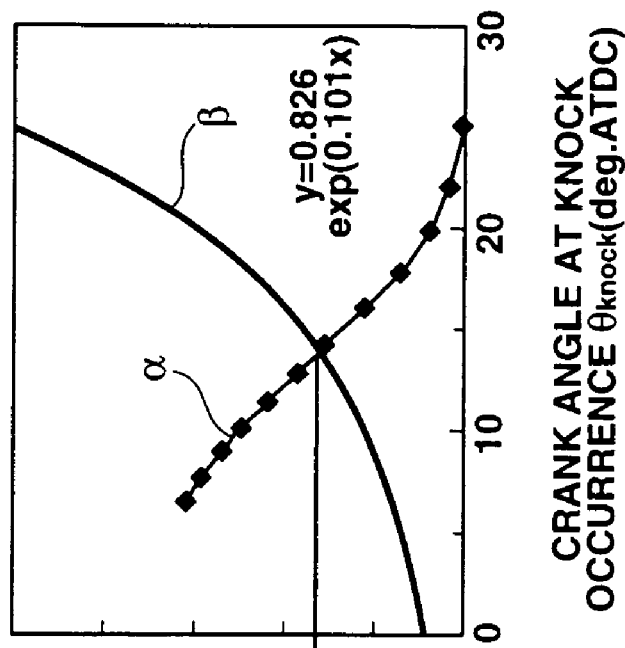
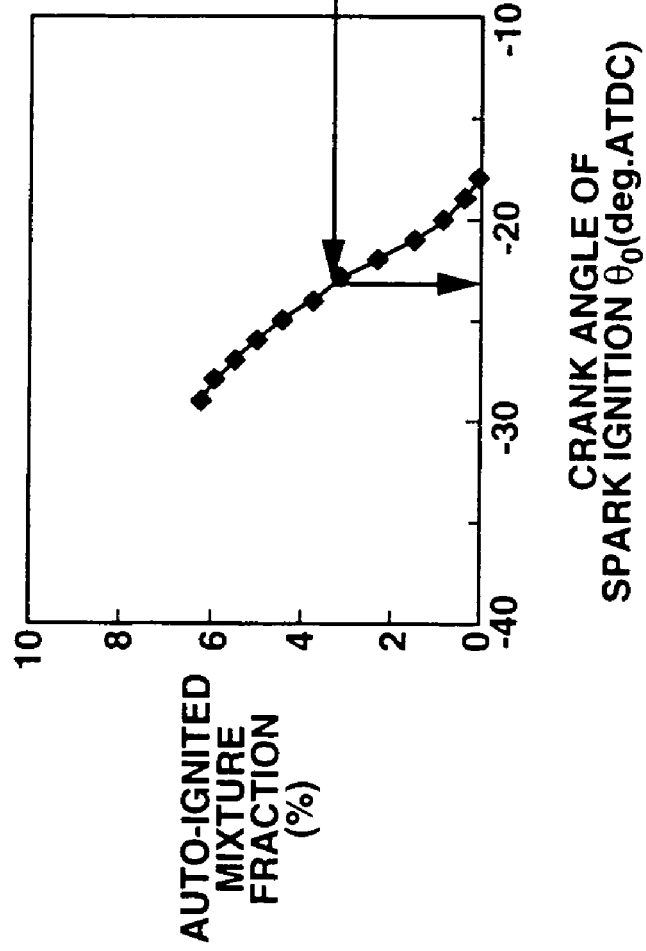
FIG.8A FIG.8B

COMBUSTION CONTROL SYSTEM AND METHOD FOR SPARK-IGNITION INTERNAL COMBUSTION ENGINE

BACKGROUND OF THE INVENTION

The present invention relates to a combustion control system and method for a spark-ignition internal combustion engine.

A spark-ignition internal combustion engine is generally operated at a higher compression ratio for improvement in thermal efficiency, but such a performance improvement can be affected by engine knock.

Hence, a knock control system that monitors the occurrence of engine knock with a knock sensor and performs feedback control on ignition timing has been proposed and already come into use so as to prevent engine knock while maximizing engine thermal efficiency.

It is herein conceivable that the engine knock could be prevented more assuredly by not only carrying out a knock avoidance operation upon detection of the engine knock but also predicting knock occurrence according to a simulation model.

Further, the ignition timing is commonly set using a prescribed ignition-timing map with reference to engine speed and power and then adjusted on detection of the engine knock. A multiplicity of actual vehicle experiments must be conducted to prepare the ignition-timing map, and the number of experiments required to prepare the ignition-timing map becomes increased with the recent application of variable mechanisms including a variable valve mechanism and an exhaust gas recirculation mechanism. This results in higher cost and greater facility for engine development. It can be however expected that the prediction of knock occurrence by a simulation model will allow an omission of many or at least some of the experiments for preparation of the ignition-timing map to thereby provide a great advantage in engine development.

In view of the foregoing, Japanese Laid-Open Patent Publication No. 7-332149 proposes a combustion control device for an internal combustion engine, capable of predicting the autoignition timing of an unburned air-fuel mixture, or equivalently, the occurrence of engine knock and controlling combustion so as to avoid the engine knock in accordance with the prediction.

SUMMARY OF THE INVENTION

When the engine knock occurs at a high intensity, there arise various problems such as a deterioration in engine durability and a unpleasant knocking sound. On the other hand, these problems do not come up when the engine knock occurs at a very low intensity. It is possible to operate the engine continuously under so-called trace knock (sporadic weak knock)" by setting the ignition timing. In other words, the engine combustion can be controlled properly by e.g. retarding the ignition timing in such a manner as to limit the knock intensity to a trace knock level.

In the above-disclosed combustion control device, however, the nonoccurrence of autoignition is made a necessary condition for the knock avoidance without any consideration of the knock intensity. It is because there has not been enough analysis made on the correlation between the autoignition prediction and the actual knock phenomenon. As a result, the ignition timing becomes overretarded to cause an undesired drop in engine thermal efficiency.

It is therefore an object of the present invention to provide a combustion control system and method for a spark-ignition internal combustion engine, by which the occurrence of engine knock can be prevented more properly based on the prediction of autoignition of an end gas, so as to maintain maximum engine thermal efficiency.

According to a first aspect of the invention, there is provided a combustion control system for a spark-ignition internal combustion engine, the system being configured to: detect engine operating conditions; predict, based on the detected engine operating conditions, autoignition timing of an end gas and an amount of heat released due to autoignition of the end gas; and control combustion to establish such a relationship between the autoignition timing and the amount of heat released due to the autoignition as to give a knock intensity not higher than a specified intensity limit.

According to a second aspect of the invention, there is provided a combustion control system for a spark-ignition internal combustion engine, the system being configured to: detect engine operating conditions; predict, based on the detected engine operating conditions, an autoignition timing of an end gas and an amount of heat released due to autoignition of the end gas; calculate a knock intensity from the autoignition timing and the amount of heat released due to the autoignition; and control combustion in the engine in such a manner that the knock intensity is lower than or equal to a specified intensity limit.

According to a third aspect of the invention, there is provided a combustion control method for a spark-ignition internal combustion engine, comprising: detecting engine operating conditions; predicting, based on the detected engine operating conditions, autoignition timing of an end gas and an amount of heat released due to autoignition of the end gas; and controlling combustion to establish such a relationship between the autoignition timing and the amount of heat released due to the autoignition as to give a knock intensity not higher than a specified intensity limit.

According to a fourth embodiment of the invention, there is provided a combustion control method for a spark-ignition internal combustion engine, comprising: detecting engine operating conditions; predicting, based on the detected engine operating conditions, autoignition timing of an end gas and an amount of heat released due to autoignition of the end gas; calculating a knock intensity from the autoignition timing and the amount of heat released due to the autoignition; and controlling combustion in the engine in such a manner that the knock intensity is lower than or equal to a specified intensity limit.

The other objects and features of the invention will also become understood from the following description.

BRIEF DESCRIPTION OF THE DRAWINGS

FIGS. 8A and 8B are diagrams of how to estimate a trace knock point on the prediction of autoignition timing and heat release amount according to one exemplary embodiment of the present invention.

DESCRIPTION OF THE EMBODIMENTS

A first embodiment of the present invention will be now explained below with reference to FIGS. 1 to 8.

Figure 1:
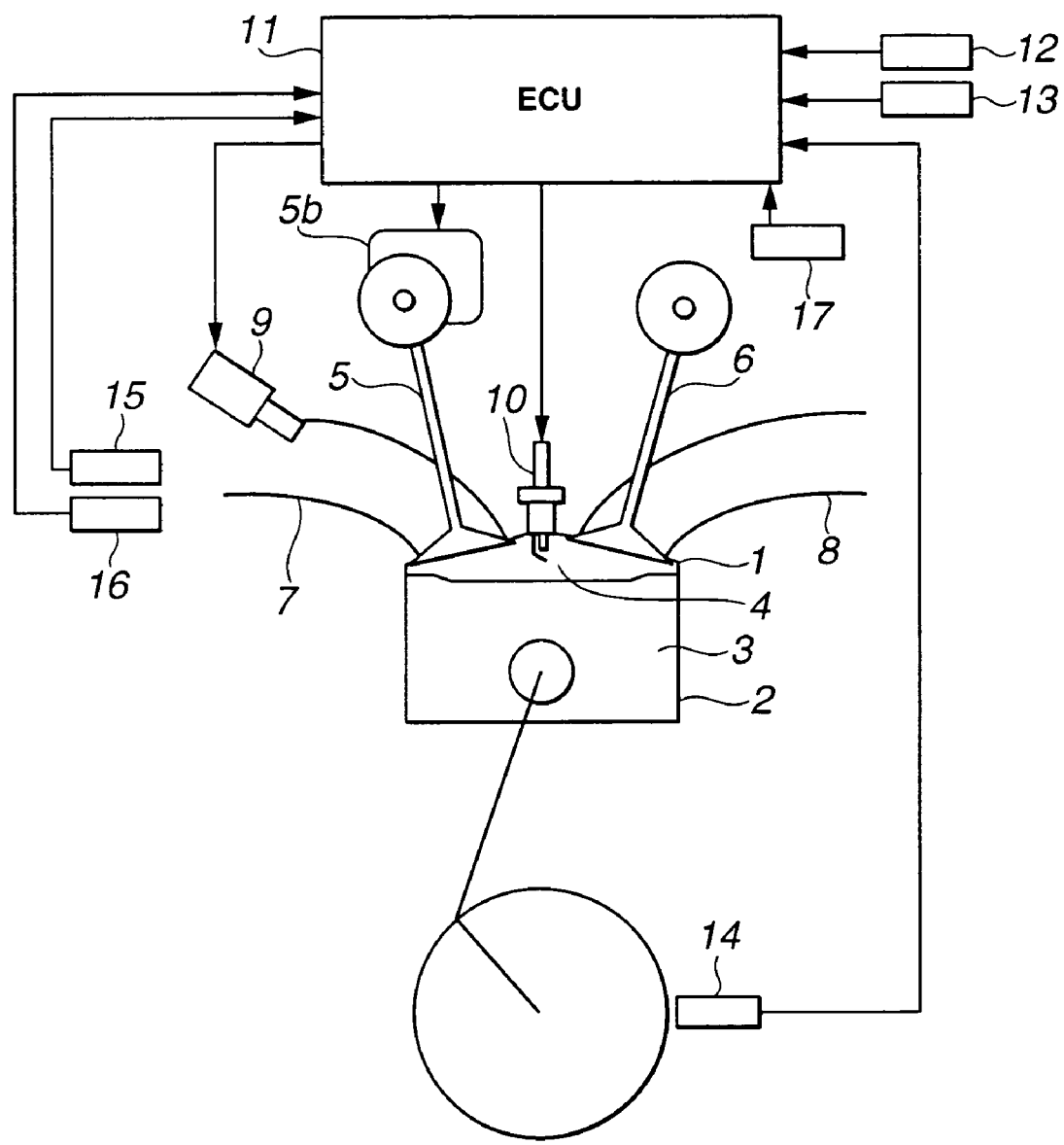
FIG. 1 is a schematic view of a spark-ignition internal combustion engine according to one exemplary embodiment of the present invention.

FIG. 1 is a schematic view of a spark-ignition internal combustion engine according to the first embodiment.

The engine has cylinder head 1, cylinder block 2, piston 3, combustion chamber 4 (defined by cylinder head 1, cylinder block 2 and piston 3), intake valve 5, valve timing control mechanism 5b, exhaust valve 6, intake port 7, exhaust port 8, fuel injection valve 9 and spark plug 10. Combustion chamber 4 is supplied with fresh air through intake valve 5 and intake port 7. For air intake control, the open and close timing of intake valve 5 is adjusted with valve timing control mechanism 5b. Fuel injection valve 9 is disposed in intake port 7 to inject an appropriate amount of fuel and thereby form a flammable air-fuel mixture in combustion chamber 4. The air-fuel mixture is ignited by spark plug 10, and the burned product gas is discharged out of combustion chamber 4 through exhaust valve 6 and exhaust port 8. The engine further includes engine control unit (ECU) 11 and various sensors, such as accelerator opening sensor 12, coolant temperature sensor 13, crank angle sensor 14, air flow meter 15, intake temperature sensor 16 and throttle sensor 17. These sensors 12 to 17 are connected to ECU 11 so that ECU 11 controls the operations of the engine integratedly in response to signals from sensors 12 to 17.

Figure 2:
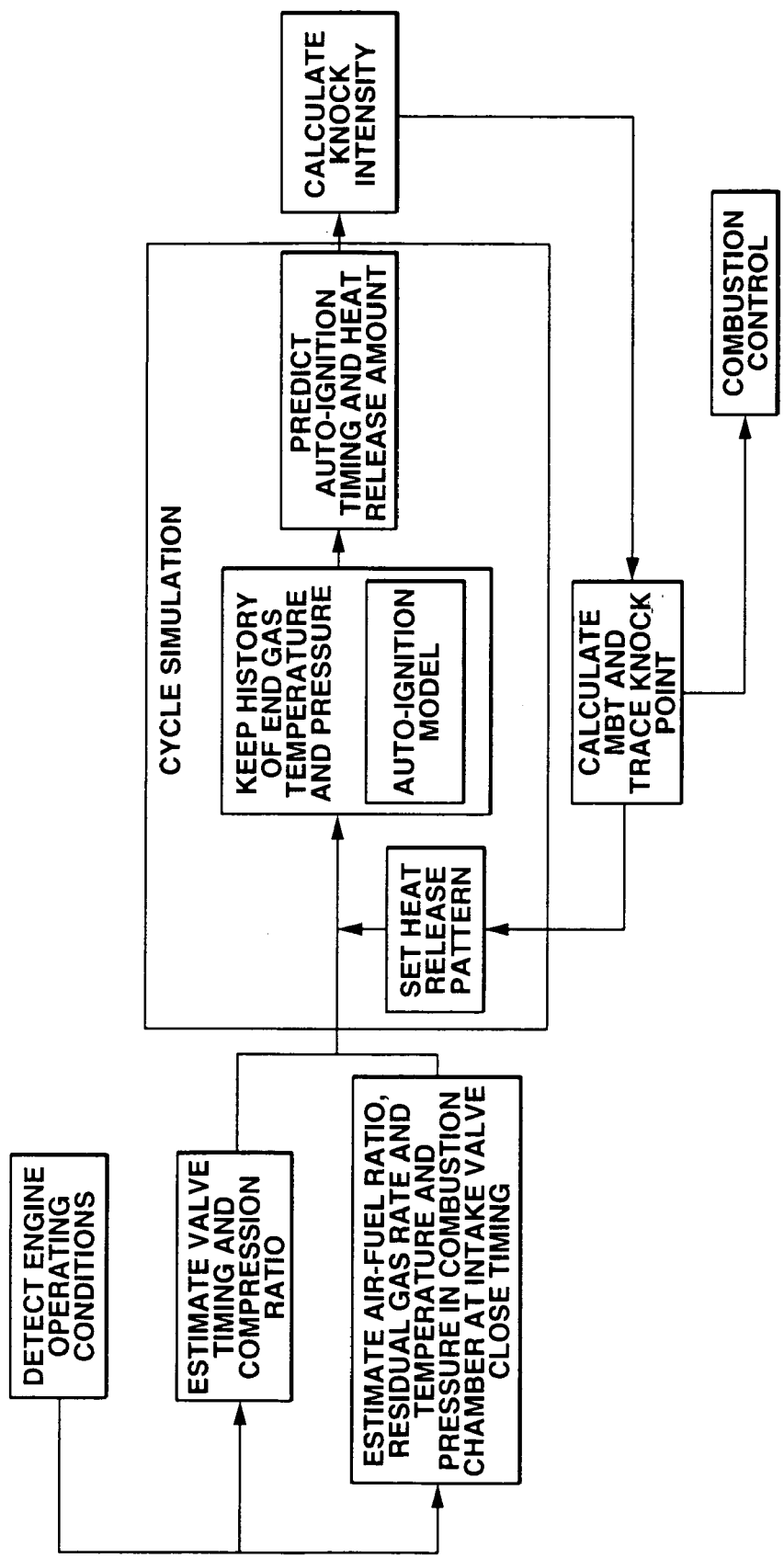
FIG. 2 is a flowchart for controlling the operations of the spark-ignition engine according to one exemplary embodiment of the present invention.

FIG. 2 is a flowchart for controlling the operations of the engine according to the first embodiment.

ECU 11 first receives the signal from sensors 12 to 17 to detect engine operating conditions including an accelerator opening, a coolant temperature, a crank angle (engine speed), an intake air amount, an intake air temperature and a throttle opening. By required signal processing and computing, ECU 11 estimates an effective compression ratio and valve timing for controlling valve timing control mechanism 5b, fuel injection valve 9 and spark plug 10. ECU 11 also estimates an air-fuel ratio, a residual gas rate and temperature and pressure in combustion chamber 4 at the close timing of intake valve 5. ECU 11 does a cycle simulation using the above estimated status values as initial parameters to predict autoignition timing of an end gas (unburned air-fuel mixture) and an amount of heat released due to autoignition of the end gas (hereinafter referred to as an "autoignition heat release amount"). The cycle simulation is done according to a two-zone combustion model and an autoignition model in the first embodiment. ECU 11 calculates a knock intensity from the predicted autoignition timing and heat release amount. ECU 11 further calculates, from the knock intensity, a trace knock point at which trace knock occurs and a minimum ignition advance for the best torque (MBT), i.e., ignition timing that presents optimal engine torque and specific fuel comsumption. Based on the trace knock point and MBT, ECU 11 performs combustion control in such a manner that the knock intensity becomes equal to or smaller than a trace knock level (an allowable limit of engine knock). ECU 11 gives feedback on the trace knock point and MBT to set a heat release pattern in the cycle simulation.

Figure 3A:
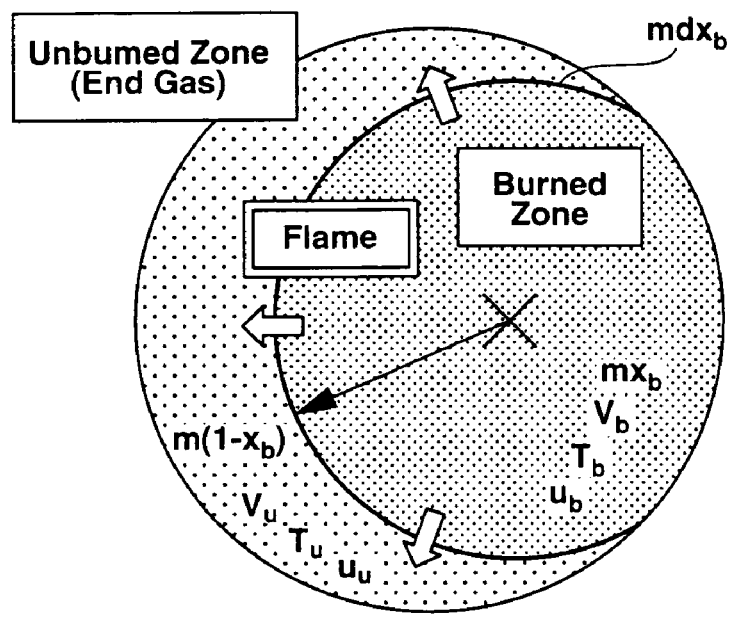
FIGS. 3A and 3B are diagrams of a two-zone combustion model.
Figure 3B:
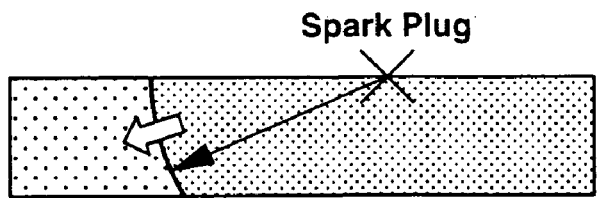

FIGS. 3A and 3B diagrams of the two-zone combustion model, showing combustion chamber 4 when viewed from above. In FIGS. 3A and 3B, the flame front of a combustion flame is indicated by a heavy line, and the position of spark plug 10 is indicated by a cross.

In the two-zone combustion model, it is assumed that the combustion flame propagates spherically from the position of spark plug 10 as shown in FIGS. 3A and 3B, so as to divide combustion chamber 4 by the flame front into two zones: a burned zone in which the burned air-fuel mixture exists and an unburned zone in which the end gas exists. During the propagation of the combustion flame, the mass and enthalpy of such a thermodynamic system is transferred from the unburned zone into the burned zone. The unburned zone becomes compressed to a high-temperature and high-pressure state under the influence of the heat release and thermal expansion in the burned zone.

In order to predict the autoignition based on the temperature and pressure of the end gas, the autoignition model is then applied to the history of the end gas temperature and pressure data in the cycle simulation. The occurrence of engine knock is judged in the case where autoignition occurs in the unburned zone before the combustion flame has propagated throughout combustion chamber 4. The autoignition timing and heat release amount are derived upon judging the knock occurrence.

The procedure of the cycle simulation by the two-zone combustion model and the autoignition model in the first embodiment will be next explained. In the following equations, the subscripts "b" and "u" are included to denote the burned zone and the unburned zone, respectively.

The energy conservation in the burned and unburned zones per unit time are given by the equations (1) and (2), respectively:

$$md(x_b u_b)+pdV_b-mdx_b h_u-dQ_{b,wall}=0 \qquad (1)$$

$$md((1-x_b)u_u)+pdV_u+mdx_b h_u-dQ_{u,wall}=0 \qquad (2)$$

where m is the mass of the air-fuel mixture, x is the mass fraction, u is the specific internal energy, i.e., the differential coefficient of internal energy, p is the pressure, V is the volume, dx is the change in mass fraction, h is the specific enthalpy and Q is the amount of heat transfer. The third term $mdx_b h_u$ of the equations (1) and (2) represents the amount of enthalpy transferred from the unburned zone to the burned zone via the flame front, and the fourth terms $dQ_{b,wall}$ and $dQ_{u,wall}$ of the equations (1) and (2) represent the amounts of heat transferred from the wall of combustion chamber 4 into the burned zone and the unburned zone, respectively.

The equation (3) holds on the assumption that combustion chamber 4 is a closed system where the change in volume per unit time is preserved according to the two-zone combustion model:

$$dV_b+dV_u=dV \qquad (3).$$

The total volume V of combustion chamber 4 may be given as a function of the crank angle θ.

The following characteristic equations (4) and (5) hold for the burned zone and the unburned zone, respectively:

$$\frac{dp}{p} + \frac{dV_b}{V_b} = \frac{dx_b}{x_b} + \frac{dR_b}{R_b} + \frac{dT_b}{T_b} \quad (4)$$

$$\frac{dp}{p} + \frac{dV_u}{V_u} = -\frac{dx_b}{1-x_b} + \frac{dR_u}{R_u} + \frac{dT_u}{T_u} \quad (5)$$

where R is the gas constant and T is the gas temperature.

Further, the mass fraction $x_b$ of the burned gas is given by the following Wiebe function (6) in the first embodiment:

$$x_b = 1 - \exp\left[-a\left(\frac{\theta - \theta_0}{\Delta\theta}\right)^{m+1}\right] \quad (6)$$

where $\theta_0$ is the crank angle of spark ignition, $\Delta\theta$ is the crank angle range during the combustion, and a and m are model constants. Alternatively, the mass fraction $x_b$ of the burned gas may be retrieved from an experimentally predetermined heat release pattern table.

The changes of states in the burned and unburned zones are estimated by solving the simultaneous equations (1) to (6) for the crank angle $\theta$. To solve the equations (1) to (6), the initial parameters are set to the above estimated status values. Also, both the fourth terms $dQ_{b,wall}$ and $dQ_{u,wall}$ of the equations (1) and (2) are taken as zero on the assumption that the cylinder gas is thermally insulated from the wall of combustion chamber 4.

The occurrence of engine knock is judged depending on whether or not the end gas is autoignited before the combustion flame has propagated throughout combustion chamber 4 according to the autoignition model as mentioned above. Then, the ignition delay $\tau$ of the end gas is calculated to predict the autoignition timing and heat released amount.

In the first embodiment, the ignition delay $\tau$ of the end gas under a certain high-temperature and high-pressure state is given by the following equation (7):

$$\tau = Ap^{-n} \exp\left(\frac{B}{T}\right) \quad (7)$$

where A, B and n are model constants. For prediction accuracy, the equation (7) needs to be applied where the end gas has already been compressed to a certain high-temperature high-pressure state due to increase in the cylinder pressure. It is thus most appropriate to apply the equation (7) to a crank angle $\theta_{pmax}$ at which the cylinder pressure becomes maximized in the course of solving the equations (1) to (6) for the crank angle $\theta$.

The end gas ignition delay $\tau$ at the crank angle $\theta_{pmax}$ is converted from the unit time to the unit angle and added to the crank angle $\theta_{pmax}$, thereby giving a predicted value $\theta_{knock}$ of the autoignition timing. Further, the predicted autoignition crank angle $\theta_{knock}$ is substituted into the equation (6) to determine the current burned mixture fraction, i.e., the current heat release amount. The current burned mixture fraction is subtracted from 1 (one), thereby giving the unburned mixture fraction at the crank angle $\theta_{knock}$, i.e., a predicted value $X_{auto-ign}$ of the autoignition heat release amount.

Herein, there is a specific relationship between the knock intensity and the autoignition timing and heat release amount as discussed below.

Figure 4A:
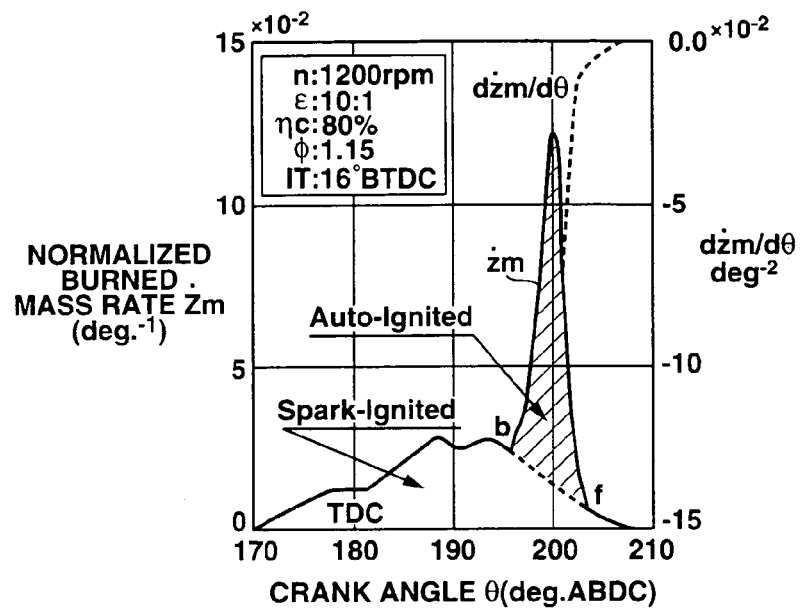
FIGS. 4A and 4B are graphs showing a relationship between knock intensity and autoignition timing and heat release amount under certain engine operating conditions.
Figure 4B:
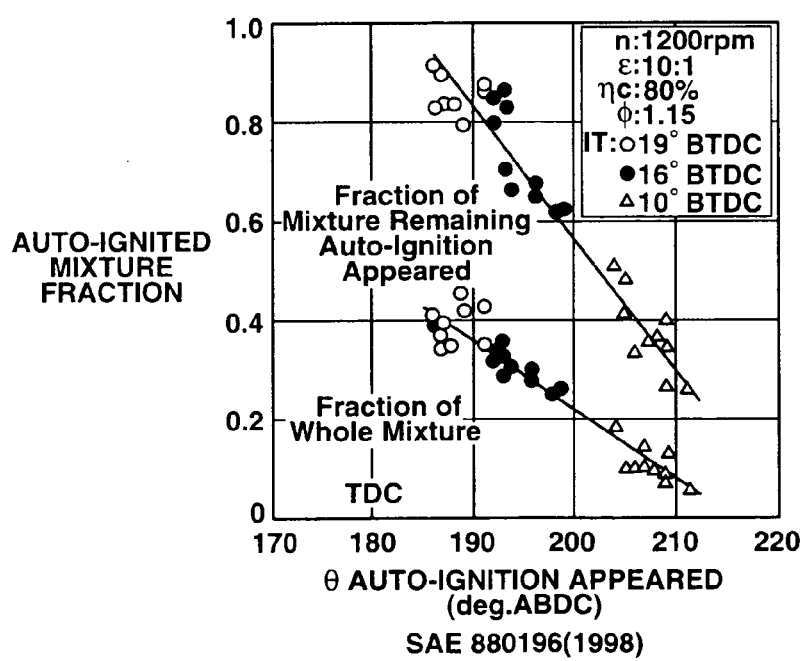

FIG. 4A is a graph showing variations in the normalized burned mass rate $\dot{Z}_m$ (deg.$^{-1}$) with respect to the crank angle $\theta$ (deg. ABDC), and FIG. 4B is a graph showing variations in the autoignition mixture fraction with respect to the crank angle at the knock occurrence $\theta_{knock}$ (deg. ABDC). It is noted that FIGS. 4A and 4B are quoted from SAE Technical Paper Series, Yasuo Takagi et al., "An Analytical Study on Knocking Heat Release and its Control in a Spark Ignition Engine," No. 880196, pp. 1–10, 1988.

As is generally known, the autoignition heat release amount increases with the spark advance toward top dead center (TDC), resulting in a higher knock intensity, when the engine operating conditions other than the ignition timing are maintained. Such a relationship between the ignition timing, the autoignition heat release amount and the knock intensity under certain engine operating conditions is clearly proved in FIGS. 4A and 4B, but it has been unclear whether the same relationship can be universally established even when not only the ignition timing but also the other engine operating condition or conditions, such as research octane number and compression ratio, are changed.

Accordingly, the present inventor has conducted the analysis of experiments on engine knock under various conditions to examine and generalize the relationship between the knock intensity and the autoignition timing and heat release amount. The analysis gives the following findings.

Figure 5:
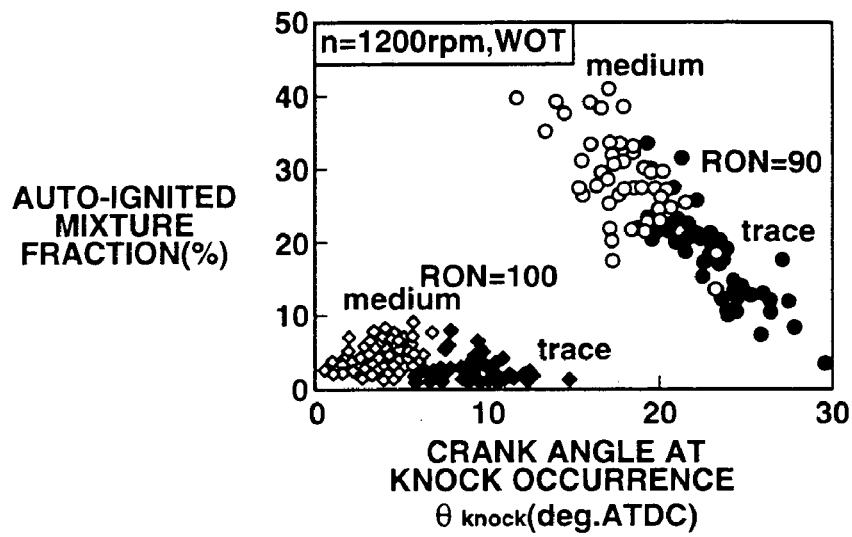
FIG. 5 is a graph showing variations in the autoignited mixture fraction with respect to the crank angle at the knock occurrence under different octane-number conditions.

FIG. 5 is a graph showing variations in the autoignited gas mixture fraction (%) with respect to the crank angle at the knock occurrence $\theta_{knock}$ (deg. ATDC) under different octane-number conditions.

When the research octane number RON is 90, the autoignited gas mixture fraction varies with the crank angle $\theta_{knock}$ in qualitatively and quantitatively the same way as in FIG. 4B. On the other hand, the autoignited gas mixture fraction stays substantially the same with respect to the crank angle $\theta_{knock}$ when the research octane number RON is 100. The crank angle $\theta_{knock}$ corresponds to the autoignition timing, while the autoignited gas mixture fraction corresponds to the autoignition heat release amount. It is thus concluded that a higher octane number results in a larger shift of the autoignition timing toward TDC and a smaller autoignition heat release amount, whereby the engine knock becomes more unlikely to occur.

Figure 6:
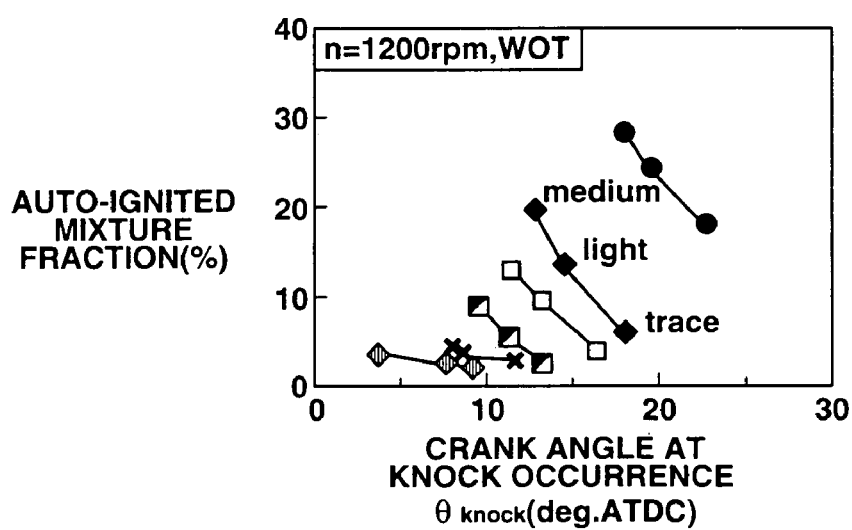
FIG. 6 is a graph showing variations in the autoignited mixture fraction with respect to the crank angle at the knock occurrence under different octane-number and compression-ratio conditions.

FIG. 6 is a graph showing variations in the autoignited gas mixture fraction (%) relative to the crank angle at the knock occurrence $\theta_{knock}$ (deg. ATDC) under different octane-number and compression-ratio conditions, obtained by averaging of the data of FIG. 5 on the cycle number. In FIG. 6, the data at a higher octane number and a lower compression ratio is plotted on the lower left side, and the data at a lower octane number and a higher compression ratio is plotted on the upper right side.

At the same knock intensity, a larger advance of the autoignition timing results in a smaller autoignition heat release amount. In other words, the knock intensity increases with the autoignition heat release amount. As the autoignition timing is advanced, the knock intensity becomes relatively high even when the autoignition heat release amount is small. It is important to consider such a relationship between the knock intensity and the autoignition timing and heat release amount in the case where the knock occurrence is judged based on the prediction of end gas autoignition.

Figure 7:
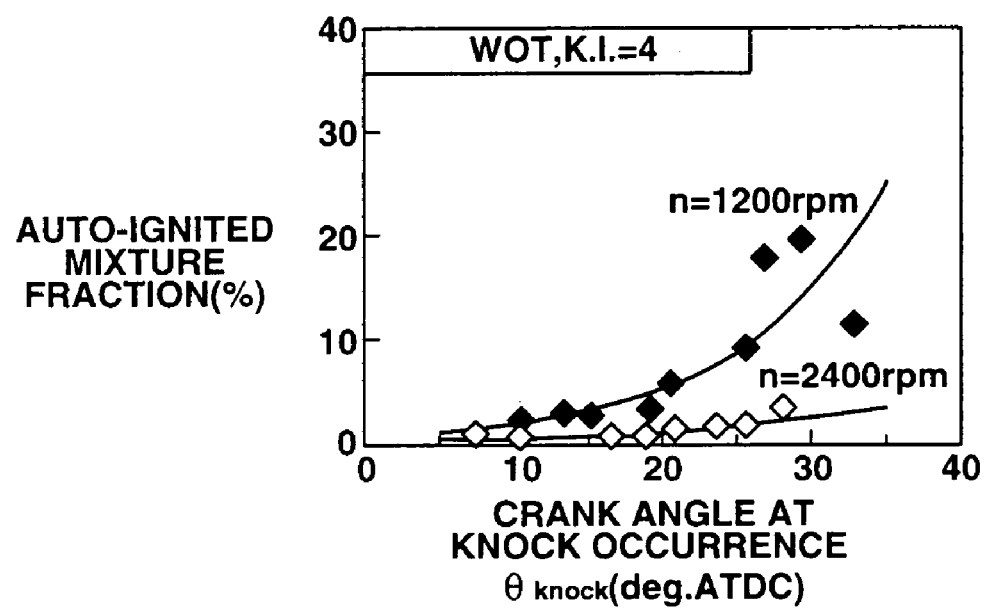
FIG. 7 is a graph showing variations in the autoignited mixture faction with respect to the crank angle at the knock occurrence under different engine-speed conditions.

FIG. 7 is a graph showing variations in the autoignited gas mixture fraction (%) relative to the crank angle at the knock occurrence $\theta_{knock}$ (deg. ATDC) under different engine-speed conditions. The data of FIG. 7 at each engine speed represents trace knock points (at which the knock sensor signal K.I. is 4).

The correlation between the autoignition timing and heat release rate at each engine speed can be well approximated to an exponential curve. Even when the autoignition heat release amount decreases with increase in the engine speed, the engine knock occurs at the same intensity. In other words, the knock intensity increases with the engine speed.

Incidentally, a correlation curve of trace knock points at an engine speed between 1200 rpm and at 2400 rpm can be obtained by interpolation of the exponential correlation curves at 1200 rpm and at 2400 rpm. It is also possible to obtain a correlation curve of trace knock points at different knock intensity.

It has been thus experimentally proved that the knock intensity increases with the autoignition heat release rate, the advance of the autoignition timing and the engine speed. Based on such a universal relationship, the knock intensity is calculated from the predicted autoignition timing $\theta_{knock}$ and heat release amount $X_{auto-ign}$ in the cycle simulation.

In the actual spark ignition engine, there is no need to perform a knock avoidance operation when the knock limit is on an advance side of MBT ignition timing, and it is most appropriate to set the spark ignition timing to the MBT ignition timing in view of the thermal efficiency. In the earlier technology, the MBT ignition timing is generally retrieved from a prescribed ignition-timing map with respect to the engine speed and load. However, the MBT ignition timing varies with the engine operating conditions, and there is a limit in setting the ignition timing using the ignition-timing map.

It is thus reasonable in the first embodiment to simulate both of MBT and the trace knock point as engine torque can be computed in the cycle simulation concurrently with the knock intensity calculation. Namely, MBT and the trace knock point are determined by estimating the knock intensity and engine torque with respect to the heat release pattern based on the Wiebe function (6) and repeating, while shifting the heat release pattern in timing, the estimation of the knock intensity and engine torque over several or dozens of times.

FIGS. 8A and 8B are schematic illustrations of how to the trace knock point. A curve α of FIG. 8B is a plot of the predicted autoignition timing $\theta_{knock}$ and heat release amount $X_{auto-ign}$ obtained by the cycle simulation, whereas a curve β of FIG. 8B is a correlation curve: y=0.826 exp(0.101x) depicting the trace knock level.

The trace knock point is defined as a point of intersection of the curves α and β of FIG. 8B, and then, converted into ignition timing presents trace knock (referred to trace knock ignition timing) as shown in FIG. 8A.

MBT is determined by simply finding through the cycle simulation an ignition timing point for the maximum engine torque.

In order for the engine to maximize engine thermal efficiency while avoiding the occurrence of heavy engine knock that can affect engine durability, the spark ignition timing is set to either one of the MBT ignition timing and the trace knock ignition timing located on a retard side.

As described above, ECU 11 predicts the autoignition timing and heat release amount based on the engine operating conditions, and then, controls the combustion to establish such a relationship between the autoignition timing and the autoignition heat release amount that the knock intensity is lower than or equal to a specified intensity limit corresponding to the trace knock level. Further, ECU 11 calculates the knock intensity from the predicted autoignition timing and heat release amount so as to limit the knock intensity to the trace knock level assuredly. By adjusting the ignition timing in view of the knock intensity, it becomes possible to operate the engine without causing an undesired deterioration in engine thermal efficiency due to the over-retardation of the ignition timing and thereby possible to maintain high engine thermal efficiency and durability.

In the first embodiment, the autoignition timing and heat release amount are predicted on the ignition delay τ of the end gas. In addition, the knock intensity is calculated in such a manner that the knock intensity increases with the autoignition heat release amount, the advance of the autoignition timing and the engine speed. This makes it possible to simplify the prediction of the autoignition timing and heat release amount and facilitate the combustion control. As the combustion control is performed by adjusting the spark ignition timing in the first embodiment, the time between the knock occurrence prediction and the actual combustion control can be reduced to avoid the engine knock more assuredly.

Next, a second embodiment of the present invention will be explained below. The second embodiment is similar to the first embodiment, except that the cycle simulation is done in consideration of the temporal characteristics of the end gas ignition delay τ as well as the heat transfer from the wall of combustion chamber 4 for high prediction accuracy.

In the second embodiment, the following Livengood-Wu integral (8) is applied to the end gas ignition delay τ:

$$\int \frac{1}{\tau} dt = 1. \tag{8}$$

The Livengood-Wu integral (8) is based on the concept that the end gas ignition delay τ varies with the passage of time.

According to the Livengood-Wo integral (8), the occurrence of end gas autoignition is judged at the time the integral of the inverse of the end gas ignition delay τ with respect to the time t becomes equal to 1 (one). The end gas ignition delay τ of the Livengood-Wu integral (8) may be expressed as a function of the temperature T and pressure p as in the equation (7). It is alternatively possible to store a preset ignition-delay map in ECU 11 and retrieve the end gas ignition delay τ from the ignition-delay map with respect the temperature T and the pressure p.

With the temporal characteristics of the end gas ignition delay τ reflected in the cycle simulation as described above, it becomes possible to insure high prediction accuracy even when there arises relatively large temperature and pressure changes during the end gas ignition delay τ.

In order to reflect the heat transfer from the wall of combustion chamber 4 in the cycle simulation and thereby insure higher prediction accuracy, a known heat transfer model for the internal combustion engine is further applied. In the second embodiment, the so-called "Woschni's heat transfer model" is adopted.

According to the Woschni's heat transfer model, the heat transfer from the wall of combustion chamber 4 is given by the following equation (9):

$$-dQ_{wall} = Ah_c(T - T_{wall}) \tag{9}$$

where A is the heat transfer area, $h_c$ is the heat transfer coefficient and $T_{wall}$ is the temperature of the combustion chamber wall.

The heat transfer coefficient $h_c$ is given by the following equations (10) and (11) according to the Woschni's heat transfer model:

$$h_c = C B^{m-1} p^m w^m T^{0.75-1.62m} \quad (10)$$

$$w = C_1 \overline{S}_p + C_2 \frac{V_d T_r}{p_r V_r}(p - p_m) \quad (11)$$

where C, $C_1$, $C_2$, and m are the model constants, B is the bore diameter, p is the cylinder pressure, T is the average in-cylinder gas temperature, $\overline{S}_p$ is the average piston speed, $V_d$ is the displacement volume, $p_m$ is the cylinder pressure at the motoring and the subscript "r" is included to denote the reference point set to e.g. the close timing of intake valve 5. The model constants $C_1$ and $C_2$ are changed in accordance to the phase of cycles of compression, combustion and expansion.

The Woschni's heat transfer model is originally designed to address average heat transfer throughout combustion chamber 4. To combine the Woschni's heat transfer model with the two-zone combustion model, it is thus necessary to allocate the amount of heat transferred from the wall of combustion chamber 4 to the burned and unburned zones in some way. In the second embodiment, it is assumed that the end gas is in a thermally insulated state during the heat release process. Based on such an assumption, the fourth term $dQ_{u,wall}$ of the equation (2) is taken as 0 (zero), and the fourth term $dQ_{b,wall}$ of the equation (1) is taken as the heat transfer amount of the equation (9).

The progression of the end gas temperature $T_u$ and pressure $p_u$ over time are thus estimated by solving the equations (1) to (6) and (8) to (11) simultaneously for the crank angle θ. In the course of solving the simultaneous equation (1) to (6) and (8) to (11), the occurrence of end gas autoignition is judged by calculating the end gas ignition delay τ from the estimated values, and then, integrating the inverse of the calculated end gas ignition delay τ with respect to time t. The predicted value $\theta_{knock}$ of the autoignition timing is given as a crank angle at which the integral becomes equal to 1 (one) as in the equation (8). The predicted value $X_{auto-ign}$ of the autoignition heat release amount is given by substituting the predicted crank angle $\theta_{knock}$ into the equation (6) and then subtracting the thus-obtained current heat release amount from 1 (one).

The knock intensity, the MBT ignition timing and the trace knock ignition timing are calculated from the predicted autoignition timing $\theta_{knock}$ and heat release amount $X_{auto-ign}$ in the same manner as in the first embodiment.

As described above, the autoignition timing and heat release amount can be predicted accurately in view of the temporal characteristics of the end gas ignition delay τ and the heat transfer from the wall of combustion chamber 4. This makes it possible to limit the knock intensity to the trace knock level more assuredly so as not to cause an undesired deterioration in engine thermal efficiency due to the overretardation of the ignition timing and thereby possible to maintain high engine thermal efficiency and durability.

Finally, a third embodiment of the present invention will be explained. The third embodiment is similar to the first and second embodiments, except that the occurrence of end gas autoignition is predicted according to another autoignition model called "elementary reaction model".

The elementary reaction model is based on the chemical kinetics in which an overall reaction is made up of a series of several tens to hundreds of elementary reactions so as to be conformable to actual physical phenomena (including molecule-to-molecule collision and reaction). The influence of not only the temperature and pressure but also the gas mixture composition and the fuel properties over the autoignition can be simulated by such an elementary reaction model. With the elementary reaction model applied to the end gas in the unburned zone, it becomes possible to predict the knock occurrence more accurately in response to the changes in valve timing, compression ratio, equivalence ratio, residual gas rate and octane number etc.

The primitive equations (1) to (6) and the Woschni's heat transfer model equations (9) to (11) are similarly used in the third embodiment.

It is now assumed that the gas mixture of combustion chamber 4 contains a mass fraction $y_i$ of the chemical species i and that the mass fraction $y_i$ of the chemical species i varies during the reaction.

The change in mass fraction $y_i$ of the chemical species i during the reaction is thus given by the following equation (12) according to the elementary reaction model:

$$dy_{i,u} = \frac{M_i}{\rho_u} \dot{\omega}_{i,u} \quad (12)$$

where $\dot{\omega}_{i,u}$ is the reaction rate of the species i, $M_i$ is the molecular weight of the species i and $\rho_u$ is the density. With the application of the Arrhenius equation to the reaction rate $\dot{\omega}_{i,u}$, the reaction rate $\dot{\omega}_{i,u}$ is expressed as a function of p, $T_u$ and $y_{i,u}$. Further, the reaction rate $\dot{\omega}_{i,u}$ can be be easily computed by CHEMKIN (a computer program commonly known for calculation of known homogeneous reaction kinetics).

The change in internal energy $du_u$ during the reaction is given by the following equation (13) according to the elementary reaction model:

$$du_u = \sum_i \frac{u_{i,u} \dot{\omega}_{i,u} M_i}{\rho_u} \quad (13)$$

Also, the change in gas constant $R_u$ during the reaction is given by the following equations (14) and (15) according to the elementary reaction model:

$$dR_u = -\frac{\tilde{R}_{uni}}{M_u^2} dM_u \quad (14)$$

$$dM_u = \sum_i \frac{M_u \dot{\omega}_{i,u} M_i}{\rho_u} \quad (15)$$

where $R_{uni}$ is the general gas constant and $M_u$ is the average molecular weight.

Although not discussed in the specification, it is also possible to apply the elementary reaction model to the burned zone so as to simulate not only engine knock, i.e., the end gas autoignition in the unburned zone but also the thermal dissociation and NO generation in the burned zone.

The progression of the end gas temperature $T_u$ and pressure $p_u$ and the mass fraction $M_i$ of the chemical species i over time is thus estimated by solving the equations (1) to (6) and (9) to (15) simultaneously for the crank angle θ. As the cycle simulation on the elementary reaction model deals with a complex system that involves sudden state changes, a high-precision, stable solver needs to be used to solve the equations (1) to (6) and (9) to (15).

The autoignition is regarded as a part of the continuous chemical reaction in the elementary reaction model. It is thus necessary to set a criterion for judging the occurrence of the autoignition. For example, the occurrence of the autoignition may judged when the end gas temperature $T_u$ becomes equal to or larger than a certain value.

The predicted value $\theta_{knock}$ of the autoignition timing is given upon judging the occurrence of autoignition based on the set criterion. Then, the predicted value $X_{auto-ign}$ of the autoignition heat release amount is given by substituting the predicted crank angle $\theta_{knock}$ into the equation (6) and subtracting the thus-obtained current heat release amount from 1 (one).

The knock intensity, the MBT ignition timing and the trace knock ignition timing are calculated from the predicted autoignition timing $\theta_{knock}$ and heat release amount $X_{auto-ign}$ in the same manner as in the first or second embodiment.

Figure 9:
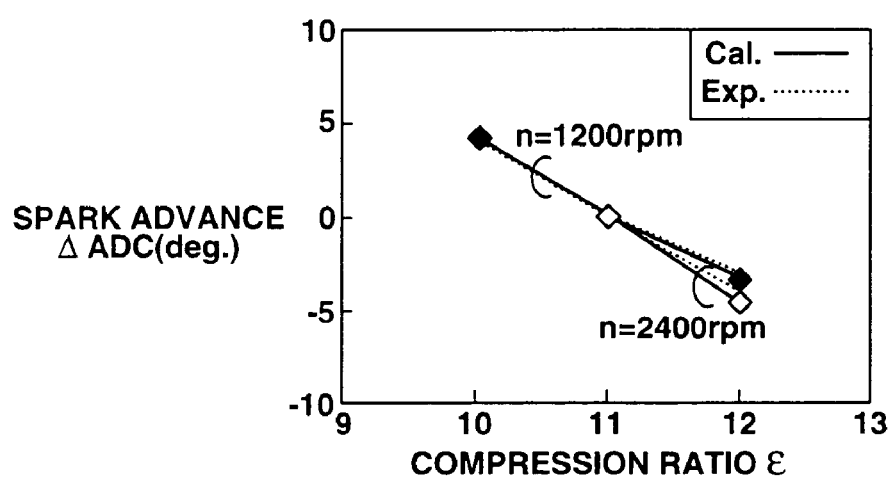
FIG. 9 is a graph showing the validity of a combustion simulation according to another exemplary embodiment of the present invention.

FIG. 9 is a graph showing how the spark advance ΔADV varies with the compression ratio ε in the actual vehicle experiment and in the cycle simulation of the third embodiment. As shown in FIG. 9, the prediction results well agree with the experimental results qualitatively and quantitatively at each engine speed. The validity of the prediction in the third embodiment is thus clearly proved in FIG. 9.

As described above, the autoignition timing and heat release amount can be predicted more accurately in response to the changes in valve timing, compression ratio, equivalence ratio, residual gas rate and octane number etc. because the influence of not only the temperature and pressure but also the gas mixture composition and the fuel properties over the end gas autoignition is reflected in the cycle simulation by the elementary reaction model. This makes it possible to limit the knock intensity to the trace knock level more assuredly so as not to cause an undesired deterioration in engine thermal efficiency due to the overretardation of the ignition timing and thereby possible to maintain high engine thermal efficiency and durability.

The entire contents of Japanese Patent Application No. 2003-126869 (filed on May 2, 2003) are herein incorporated by reference.

Although the present invention has been described with reference to specific embodiments of the invention, the invention is not limited to the above-described embodiments. Various modification and variation of the embodiments described above will occur to those skilled in the art in light of the above teaching. The scope of the invention is defined with reference to the following claims.

What is claimed is:

1. A combustion control system for a spark ignition internal combustion engine, the system being configured to:
   detect engine operating conditions;
   predict, based on the detected engine operating conditions, autoignition timing of an end gas and an amount of heat released due to autoignition of the end gas; and
   control combustion to establish such a relationship between the autoignition timing and the amount of heat released due to the autoignition as to give a knock intensity not higher than a specified intensity limit.

2. A combustion control system according to claim 1, wherein the knock intensity is calculated such that the knock intensity increases as the amount of heat released due to the autoignition is increased and as the autoignition timing is advanced.

3. A combustion control system according to claim 2, wherein the knock intensity is calculated such that the knock intensity increases with engine speed.

4. A combustion control system according to claim 1, wherein the specified intensity limit corresponds to a trace knock level.

5. A combustion control system according to claim 1, wherein the combustion is controlled by adjusting ignition timing.

6. A combustion control system according to claim 1, wherein the autoignition timing and the amount of heat released due to the autoignition are predicted by estimating an ignition delay of the end gas.

7. A combustion control system according to claim 1, wherein the occurrence of the autoignition is predicted by integrating the inverse of an ignition delay of the end gas to estimate the autoignition timing and the amount of heat released due to the autoignition.

8. A combustion control system according to claim 1, wherein the occurrence of the autoignition is predicted by an elementary reaction model to estimate the autoignition timing and the amount of heat released due to the autoignition.

9. A combustion control method for a spark-ignition internal combustion engine, comprising:
   detecting engine operating conditions;
   predicting, based on the detected engine operating conditions, autoignition timing of an end gas and an amount of heat released due to autoignition of the end gas; and
   controlling combustion to establish such a relationship between the autoignition timing and the amount of heat released due to the autoignition as to give a knock intensity not higher than a specified intensity limit.

10. A combustion control method according to claim 9, further comprising:
    computing an engine torque while calculating the knock intensity; and
    determining trace knock ignition timing and MBT ignition timing based on the knock intensity and the engine torque,
    wherein said controlling includes setting spark ignition timing to either one of the MBT ignition timing and the trace knock ignition timing located on a retard side.

11. A combustion control method according to claim 9, wherein the knock intensity is calculated such that the knock intensity increases as the amount of heat released due to the autoignition is increased, as the autoignition timing is advanced and as engine speed is increased.

12. A combustion control system for a spark-ignition internal combustion engine, the system being configured to:
    detect engine operating conditions;
    predict, based on the detected engine operating conditions, an autoignition timing of an end gas and an amount of heat released due to autoignition of the end gas;
    calculate a knock intensity from the autoignition timing and the amount of heat released due to the autoignition; and
    control combustion in the engine in such a manner that the knock intensity is lower than or equal to a specified intensity limit.

13. A combustion control system according to claim 12, wherein the knock intensity is calculated such that the knock intensity increases as the amount of heat released due to the autoignition is increased and as the autoignition timing is advanced.

14. A combustion control system according to claim 13, wherein the knock intensity is calculated such that the knock intensity increases with engine speed.

15. A combustion control system according to claim 12, wherein the specified intensity limit corresponds to a trace knock level.

16. A combustion control system according to claim 12, wherein the combustion is controlled by adjusting ignition timing.

17. A combustion control system according to claim 12, wherein the autoignition timing and the amount of heat released due to the autoignition are predicted by estimating an ignition delay of the end gas.

18. A combustion control system according to claim 12, wherein the occurrence of the autoignition is predicted by integrating the inverse of an ignition delay of the end gas to estimate the autoignition timing and the amount of heat released due to the autoignition timing.

19. A combustion control system according to claim 12, wherein the occurrence of the autoignition is predicted by an elementary reaction model to estimate the autoignition timing and the amount of heat released due to the autoignition.

20. A combustion control method for a spark-ignition internal combustion engine, comprising:

detecting engine operating conditions;

predicting, based on the detected engine operating conditions, autoignition timing of an end gas and an amount of heat released due to autoignition of the end gas;

calculating a knock intensity from the autoignition timing and the amount of heat released due to the autoignition; and controlling combustion in the engine in such a manner that the knock intensity is lower than or equal to a specified intensity limit.

21. A combustion control method according to claim 20, further comprising:

computing an engine torque while calculating the knock intensity; and determining trace knock ignition timing and MBT ignition timing based on the knock intensity and the engine torque, wherein said controlling includes setting spark ignition timing to either one of the trace knock ignition timing and the MBT ignition timing located on a retard side.

22. A combustion control method according to claim 20, wherein the knock intensity is calculated such that the knock intensity increases as the amount of heat released due to the autoignition is increased, as the autoignition timing is advanced and as engine speed is increased.

* * * * *